(12) United States Patent
Teras et al.

(10) Patent No.: US 7,527,815 B2
(45) Date of Patent: *May 5, 2009

(54) METHOD FOR REDUCING ACRYLAMIDE IN CORN-BASED FOODS, CORN-BASED FOODS HAVING REDUCED LEVELS OF ACRYLAMIDE, AND ARTICLE OF COMMERCE

(75) Inventors: Lee Michael Teras, Cincinnati, OH (US); Stephen Paul Zimmerman, Wyoming, OH (US); David Vincent Zyzak, Mason, OH (US); Peter Yau Tak Lin, Liberty Township, OH (US); Marko Stojanovic, Cincinnati, OH (US); Robert Alan Sanders, Fairfield, OH (US); Maria Dolores Martinez-Serna Villagran, Mason, OH (US); John Keeney Howie, Oregonia, OH (US); Richard Gerald Schafermeyer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/603,279

(22) Filed: Jun. 25, 2003

(65) Prior Publication Data
US 2004/0265429 A1 Dec. 30, 2004

(51) Int. Cl.
| | |
|---|---|
| A23B 7/155 | (2006.01) |
| A23J 3/34 | (2006.01) |
| A23L 1/217 | (2006.01) |
| A23L 3/3571 | (2006.01) |
| A23L 1/212 | (2006.01) |
| A23L 1/00 | (2006.01) |

(52) U.S. Cl. .................. 426/52; 426/549; 426/61; 426/438; 426/615; 426/618; 426/496

(58) Field of Classification Search ............ 426/52, 426/106, 618, 627, 808, 656, 438
See application file for complete search history.

(56) References Cited

U.S. PATENT DOCUMENTS 2,490,431 A  12/1949  Greene et al.

(Continued)

FOREIGN PATENT DOCUMENTS

KR  0595873  7/2006

(Continued)

OTHER PUBLICATIONS

Borek, D., et al. "Sequence of Analysis of Enzymes with Asparaginase Activity." ActaBiochimica Polonica, vol. 48, Issue 4, pp. 893-902, 2001.*

(Continued)

*Primary Examiner*—Keith D Hendricks
*Assistant Examiner*—Viren Thakur
(74) *Attorney, Agent, or Firm*—Adam W. Borgman; Kim William Zerby; Steven W. Miller

(57) ABSTRACT

A method for the reduction of acrylamide in corn-based food products, corn-based food products having reduced levels of acrylamide, and an article of commerce. In one aspect, the method comprises reducing the level of asparagine in a corn-based food material before final heating (e.g., cooking). In another aspect, the method comprises adding to a corn-based food material an enzyme capable of hydrolyzing the amide group of free asparagine. In yet another aspect, an article of commerce communicates to the consumer that a corn-based food product has reduced or low levels of acrylamide or asparagine.

9 Claims, 3 Drawing Sheets

U.S. PATENT DOCUMENTS

| | | | |
|---|---|---|---|
| 2,704,257 | A | 3/1955 | De Sollano et al. |
| 2,759,832 | A | 8/1956 | Cording et al. |
| 2,780,552 | A | 2/1957 | Willard et al. |
| 2,905,559 | A | 9/1959 | Andersen et al. |
| 3,085,020 | A | 4/1963 | Backinger et al. |
| 3,369,908 | A | 2/1968 | Gonzales et al. |
| 3,690,895 | A | 9/1972 | Amadon et al. |
| 3,917,866 | A | 11/1975 | Purves et al. |
| 3,987,210 | A | 10/1976 | Cremer |
| 3,998,975 | A | 12/1976 | Liepa |
| 4,210,594 | A | 7/1980 | Logan et al. |
| 4,985,269 | A | 1/1991 | Irvin et al. |
| 5,356,646 | A | 10/1994 | Simic-Glavaski et al. |
| 5,464,642 | A | 11/1995 | Villagran et al. |
| 5,464,643 | A | 11/1995 | Lodge |
| 5,558,886 | A | 9/1996 | Martinez-Bustos et al. |
| 6,066,353 | A | 5/2000 | Villagran et al. |
| 6,068,873 | A | 5/2000 | Delrue et al. |
| 6,287,622 | B1 | 9/2001 | Villagran et al. |
| 6,528,768 | B1 | 3/2003 | Simic-Glavaski et al. |
| 2004/0058054 | A1 * | 3/2004 | Elder et al. ................. 426/658 |

FOREIGN PATENT DOCUMENTS

| | | |
|---|---|---|
| WO | WO 96/01572 | 1/1996 |
| WO | WO 01/91581 | 12/2001 |
| WO | WO 2004/004484 | 1/2004 |

OTHER PUBLICATIONS

FAO/WHO Consultation on the Health Implications of Acrylamide in Food: Summary Report; Geneva Switzerland, Jun. 25-27, 2002.

Talburt & Smith; "Potato Processing"; 4th Edition, 1987, pp. 535-646.

Watson, S.A.; "Corn: Chemistry and Technology"; American Association of Cereal Chemists, 1987; pp. 410-420.

Zyzak, David A. et al.; "Acrylamide Formation Mechanism in Heated Foods"; Journal of Agricultural and Food Chemistry; vol. 51, No. 16, pp. 4782-4787, Jul. 2003.

Biederman, Maurus, et al.; "Methods for Determining the Potential of Acrylamide Formation and Its Elimination in Raw Materials for Food Preparation, such as Potatoes"; Official Food Control Authority of the Canton of Zurich.

Biederman, Maurus, et al.: "Experiments on Acrylamide Formation and Possibilities to Decrease the Potential of Acrylamide Formation in Potatoes"; Official Food Control Authority of the Canton of Zurich.

Nielsen, Monk; "Enzyme Technology For Production of Protein Based Flavours"; Novo Nordisk; 1995.

WWW.Foodstandards.gov.uk; "Food Standards Agency Study of Acrylamide in Food Background Information and Research Findings"; Press Briefing May 17, 2002.

European Commission; Health & Consumer Protection Directorate—General; "Opinion of the Scientific Committee on Food on new findings regarding the presence of acrylamide in food"; Jul. 3, 2002.

Institute of Food Science & Technology (UK); "Additional Research on Acrylamide in Food Essential, Scientists Declare"; Joint Press Release FAO/WHO/51; Jun. 27, 2002.

www.cspinet.org; Center for Science in the Public Interest; "New Tests Confirm Acrylamide in American Foods"; Jun. 25, 2002.

Tareke, Eden, et al.; "Analysis of Acrylamide, a Carcinogen Formed in Heated Foodstuffs"; Journal of Agricultural and Food Chemistry, pp. A-I.

Sanders, R.A., et al.; "An LC/MS Acrylamide Method and It's Use in Investigating the Role of Asparagine"; Presented at the Association of Analytical Communities ; Sep. 2002.

Zyzak, David; "Acrylamide: Mechanism of Formation in Heated Foods": Presented to the FDA Food Advisory Committee; Feb. 24, 2003.

* cited by examiner

Figure 2 Mode of action for asparaginase

METHOD FOR REDUCING ACRYLAMIDE IN CORN-BASED FOODS, CORN-BASED FOODS HAVING REDUCED LEVELS OF ACRYLAMIDE, AND ARTICLE OF COMMERCE

FIELD OF INVENTION

The present invention relates to the reduction of acrylamide in corn-based food products and to corn-based food products having reduced levels of acrylamide. The invention further relates to an article of commerce.

BACKGROUND OF THE INVENTION

Since the dawn of civilization, carbohydrate-containing foods have been a staple in man's diet. Today, carbohydrate-containing foods such as breads, breakfast cereals, biscuits, crackers, cookies, French fries, cooked starchy vegetables, taco shells, and snack foods are popularly consumed. Many of these carbohydrate-containing foods are corn-based or contain corn-based ingredients. Although such corn-based food products have been part of the human diet for countless years, researchers have only recently discovered that many of these foods contain acrylamide.

In April 2002, the Swedish National Food Administration and researchers from Stockholm University announced their findings that acrylamide, a potentially cancer-causing chemical, is formed in many types of cooked foods. Acrylamide has a carcinogenic potency in rats that is similar to that of other carcinogens in food, but for humans, the relative potency in food is not known. Only limited human population data are available for acrylamide and these provide no evidence of cancer risk from occupational exposure. (*FAO/WHO Consultation on the Health Implications of Acrylamide in Food: Summary Report*; Geneva, Switzerland, 25-27 Jun. 2002.)

Although further research is needed to assess what health effects, if any, may result from human consumption of acrylamide at the levels commonly found in such foods, many consumers have voiced concern. Accordingly, it is an object of the present invention to provide a method for reducing the level of acrylamide in corn-based foods. It is also an object of the present invention to provide corn-based food products having reduced levels of acrylamide. Further, it is an object of the present invention to provide an article of commerce that communicates to the consumer that a corn-based food product has reduced or low levels of acrylamide.

SUMMARY OF THE INVENTION

In one aspect, the present invention provides a method for reducing the level of acrylamide in a corn-based food product. In one embodiment, the method comprises adding an asparagine-reducing enzyme to the corn-based food material before heating.

In another aspect, the present invention provides a method for reducing the level of asparagine in a corn-based food material. In one embodiment, the method comprises adding an asparagine-reducing enzyme to the corn-based food material before heating.

In another aspect, the present invention provides corn-based food products having reduced levels of acrylamide.

In yet another aspect, the present invention provides an article of commerce that communicates to the consumer that a corn-based food product has reduced or low levels of acrylamide or of asparagine.

All documents cited herein are, in relevant part, incorporated herein by reference; the citation of any document is not to be construed as an admission that it is prior art with respect to the present invention.

BRIEF DESCRIPTION OF THE DRAWINGS

FIG. 1 sets forth the proposed reaction mechanism by which acrylamide forms from asparagine and a carbonyl source (such as glucose). $R_1$ and $R_2$ can=H, $CH_3$, $CH_2OH$, $CH_2(CH_2)_nCH_3$, or any other component making up a reducing sugar; n can be any integer less than 10.

FIG. 2 sets forth the proposed reaction mechanism by which asparaginase reacts with asparagine to prevent the formation of acrylamide.

FIG. 3 sets forth a sample chromatogram for LC analysis of asparagine and aspartic acid. The x-axis represents retention time and the y-axis represents response.

DETAILED DESCRIPTION OF THE INVENTION

Applicants have discovered that asparagine, a naturally occurring amino acid found in virtually all living systems, can form acrylamide when heated. Thus, foods richer in asparagine, when heated, tend to contain higher levels of acrylamide; this is especially the case when asparagine-containing foods are heated in the presence of reducing sugars. Formation of acrylamide has also been found to be higher when foods are cooked to a lower final moisture content.

Figure 1:
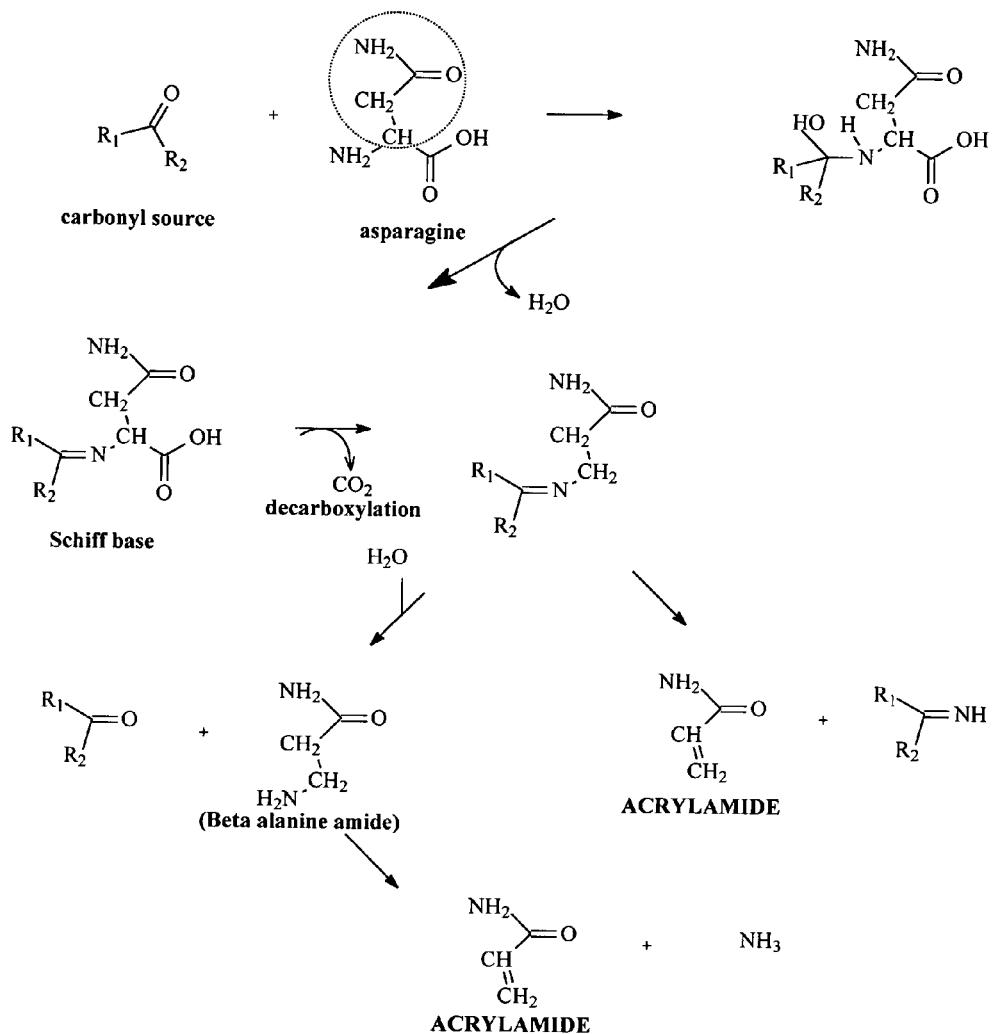
FIG. 1.

While not being limited by theory, it is believed that acrylamide forms in corn-based food products via the reaction mechanism set forth in FIG. 1. It is believed that the alpha-amine group of free asparagine reacts with a carbonyl source, forming a Schiff base. Under heat, the Schiff base adduct decarboxylates, forming a product that can either: (1) hydrolyze to form beta-alanine amide (which can, under heat, further degrade to form acrylamide) or (2) decompose to form acrylamide and the corresponding imine. (Applicants have discovered that the circled precursor atoms comprise the carbons and nitrogens in acrylamide.)

Accordingly, Applicants have further discovered that acrylamide formation in heated food products can be reduced by removing the asparagine or converting the asparagine in the food to another substance before cooking. Thus, when corn-based foods containing reduced levels of asparagine are heated, the amount of acrylamide formed is reduced.

Figure 2:
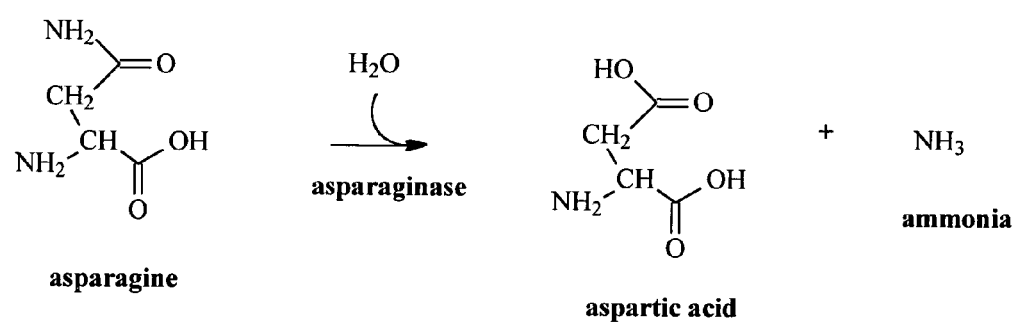
FIG. 2.

Applicants have found that adding an enzyme that hydrolyzes the amide group on the side chain of asparagine prior to heating (e.g., cooking) the food reduces the level of acrylamide present in the finished food product. While not being limited by theory, it is believed that the addition of such an enzyme degrades the side chain of asparagine, thus preventing the asparagine from forming acrylamide. In doing so, the amide bond is hydrolyzed and asparagine is converted to aspartic acid. This reaction mechanism is set forth in FIG. 2.

The advantages of using enzymes in corn-based food processing are numerous. These advantages include: (a) they are natural, nontoxic substances; (b) they generally catalyze a given reaction without causing unwanted side reactions; (c) they are active under very mild conditions of temperature and pH; (d) they are active at low concentrations; (e) the rate of reaction can be controlled by adjusting temperature, pH, and the amount of enzyme employed; and (f) they can be inactivated after the reaction has proceeded to the desired extent. (*Food Chemistry*, 4th Ed., Owen R. Fennema, Ed., Marcel Dekker, Inc., New York, 1985, pp. 427, 433.)

A. Method for Reduction of Acrylamide in Corn-Based Food Products

In one aspect, the present invention provides a method for the reduction of acrylamide in a corn-based food product. In one embodiment, the method comprises reducing the level of asparagine in a corn-based food material before final heating (e.g., cooking). In another aspect, the method comprises adding to a corn-based food material an enzyme capable of hydrolyzing the amide group of free asparagine. The preferred enzyme is asparaginase.

In another aspect, the present invention provides a method for the reduction of asparagine in a corn-based food product. In one embodiment, the method comprises adding to a corn-based food material an enzyme capable of hydrolyzing the amide group of free asparagine. The preferred enzyme is asparaginase.

In a preferred embodiment, the present invention provides a method for reducing the level of acrylamide in a corn-based food product, comprising:

(1) adding an asparagine-reducing enzyme to a corn-based food material, wherein said corn-based food material comprises asparagine;
(2) optionally mixing the enzyme with the corn-based food material;
(3) allowing a sufficient time for the enzyme to react with the asparagine;
(4) optionally deactivating or optionally removing the enzyme; and
(5) heating the corn-based food material to form the final corn-based food product.

1. Adding an Asparagine-Reducing Enzyme to a Corn-Based Food Material, wherein Said Corn-Based Food Material Comprises Asparagine As used herein, "asparagine-reducing enzyme" includes any enzyme capable of reducing the level of asparagine in a corn-based food material. In one embodiment, the asparagine-reducing enzyme is an enzyme capable of hydrolyzing the amide group of free asparagine. A preferred enzyme for use herein is asparaginase. A preferred source of asparaginase is Sigma-Aldrich, catalog #A2925. Another preferred enzyme for use herein is glutaminase.

As used herein, the terms "asparagine-reducing enzyme" and "enzyme" include one or more enzymes; for example, a mixture of two or more enzymes is encompassed by the terms. For example, deamidases that have asparagine-reducing functionality are included in the terms.

As used herein, "corn-based" means comprising from 50% to 100% corn.

As used herein, "corn-based food material" includes, but is not limited to, any type of asparagine-containing corn-based food, corn-based food product, corn-based food ingredient, or mixtures thereof.

The corn-based food material can be in any suitable form, including raw, dried, processed, or pre-treated. Suitable methods of pre-treating the corn-based food material can include, but are not limited to, blanching, steaming, boiling, chopping, macerating, comminuting, reducing the particle size, drying with heat, and combinations thereof. For instance, the corn-based food material can include whole kernel, cracked, on or off the cob, partial kernels, a granular consistency, a powder consistency (e.g., such as with a meal or flour), cooked kernels that have been pre-treated in any way (e.g., chemically processed with base treatment such as lime, for instance in making masa or nixtamal), and combinations thereof. In one embodiment, the corn-based food material can be a corn-based food that is used in the preparation of another food.

Any suitable corn can be used herein. The type of corn can include, but is not limited to, dent, flint, flour, sweet, pop, pod, waxy varieties, and combinations hereof. The corn color can include, but is not limited to, yellow, white, blue, and combinations hereof. The corn be can derived from natural selection, hybridization, be genetically modified, and combinations thereof.

As used herein, "adding" the enzyme to the corn-based food material includes, but is not limited to, any means of bringing the asparagine and the enzyme together.

The enzyme can be added to the corn-based food material in any suitable form. For instance, the enzyme may be added as a powder or in the form of a solution (e.g., dissolved in water). Furthermore, the enzyme may be added to the corn-based food material in any suitable manner, such as directly (for example, sprinkled, poured, or sprayed on the corn-based food material) or indirectly. In one embodiment, the enzyme is admixed with another food material that does not contain asparagine, then the resulting mixture is added to the asparagine-containing corn-based food material.

In another embodiment, the enzyme is added to a substrate (e.g., starch, silica); this facilitates the homogeneous addition of the enzyme to the corn-based food material. The amount of enzyme added is relatively small in comparison to the amount of corn-based food material to which the enzyme is added. Thus, by adding enzyme as part of a diluted substrate system, a greater amount of enzyme/substrate blend can be added to the corn-based material to achieve the same enzyme level.

In another embodiment, at least a portion of the asparagine is extracted from the corn-based food material, the resulting extract is treated with enzyme, then at least a portion of the extract is added back into at least a portion of the corn-based food material; for example, the enzyme may be added to the stream, or the stream may be pumped through a bed or column of immobilized enzyme (enzyme either adsorbed or chemically bonded to a substrate, preferably an inert substrate, e.g., pieces of plastic or beads in a column).

Furthermore, the enzyme can be added to the corn-based food material at any suitable stage of processing, or at more than one stage of processing. For instance, enzyme can be added before, during, or after the processing or manufacture of the corn-based food material; enzyme can be added to a food product before, during, or after the addition of the corn-based food material to the other food product ingredients; enzyme can be added to the food product after it is prepared but before final heating; and variations and combinations thereof. For example, enzyme may be admixed with dough ingredients during the mixing of a corn dough for use in preparing fabricated corn snacks.

The amount of enzyme to add can depend upon the level of asparagine reduction, and accordingly the level of acrylamide reduction, that is desired. The amount of enzyme to add can also depend upon the amount of asparagine present in the corn-based food material; corn-based food materials higher in asparagine will generally require increased levels of enzyme or increased reaction time to achieve the same level of acrylamide reduction. The amount of enzyme to add can also depend upon the particular enzyme used (for example, the particular enzyme's ability to degrade asparagine) and the particular corn-based food material treated.

Enzymes are marketed by units of activity, rather than by weight or volume. Thus, the effective amount of enzyme required to achieve the desired level of acrylamide reduction in the finished corn-based food product will depend upon the activity of the particular enzyme product used.

One skilled in the art will be able to determine the effective amount of enzyme based upon the specific corn-based food material, the specific enzyme, the enzyme's specific activity, and the desired result.

2. Optionally Mixing the Enzyme with the Corn-Based Food Material

Optionally but preferably, the enzyme is thoroughly mixed with the corn-based food material. Any suitable method of mixing can be used. In one embodiment, mixing is carried out simultaneously with the maceration of the corn-based food material and the addition of the enzyme.

3. Allowing a Sufficient Time for the Enzyme to React with the Asparagine

The amount of time needed for the enzyme to react with the asparagine will depend upon factors including, but not limited to, the desired level of acrylamide reduction, the characteristics of the particular corn-based food material (e.g., chemical composition, amount of asparagine present, particle size), and the particular enzyme added. Preferably, the enzyme is allowed to react for a sufficient amount of time to result in a corn-based food material wherein the level of asparagine has been reduced by at least about 10%, preferably at least about 30%, more preferably at least about 50%, still more preferably at least about 70%, and even more preferably at least about 90%. In general, the longer the enzyme is allowed to react, the greater the level of asparagine reduction and thus the greater the level of acrylamide reduction. The step of allowing a sufficient time for the enzyme to react can be carried out in any suitable manner; for example, it can be carried out simultaneously with adding the enzyme to the corn-based food material, mixing the enzyme with the corn-based food material, or combinations thereof.

As known in the art, pH and temperature are factors that affect enzymatic activity. One skilled in the art should readily be able to determine optimal conditions of these and other parameters (e.g., water content). In addition, optimal pH and temperature conditions for specific enzymes are typically available in the literature and/or from enzyme suppliers.

4. Optionally Deactivating or Optionally Removing the Enzyme

After the enzyme has reacted to the desired extent, it can optionally be inactivated or removed from the corn-based food material. When an enzyme that is safe for consumption (e.g., naturally occurring and found in common corn-based foods) is used, one may choose not to deactivate or remove the enzyme. Alternatively, the enzyme can be deactivated by any suitable means that inactivates the enzyme. For example, the enzyme can be deactivated through the use of heat, pH adjustment, treatment with a protease, or combinations thereof. Furthermore, the enzyme can be removed from the corn-based food material by any suitable means including, but not limited to, extraction. The enzyme can be deactivated, removed, or subjected to a combination of deactivation and removal.

Enzyme deactivation can occur simultaneously with other processing steps. For instance, the enzyme deactivation step can be part of the corn dry or wet mill processing steps. In one embodiment, the addition of high pH lime-water during the production of nixtamal denatures the enzyme. In another embodiment, the enzyme is deactivated during the heated drying step of the nixtamal process.

5. Heating the Corn-Based Food Material to Form the Finished Corn-Based Food Product The corn-based food material can then be heated in the usual manner, such as by baking, frying, extruding, drying (e.g., via vacuum oven or drum dryer), puffing, or microwaving. At least a portion of the enzyme may be added to the corn-based food material during the heating step. Deactivating the enzyme may occur through heating, thus the optional deactivation step and the cooking step may be carried out simultaneously. Heat processing via cooking can denature and inactivate the enzyme such that the corn-based food material is not subjected to continuing enzymatic activity. Furthermore, at least a portion of the time allowed for enzymatic reaction may be carried out during the heating step.

As used herein the term "finished corn-based food product" or "corn-based food product" includes, but is not limited to, corn-based foods ready for consumption and corn-based foods to be used as ingredients to prepare other corn-based foods.

Preferably, the level of acrylamide in the finished corn-based food product is reduced by at least about 10%, preferably at least about 30%, more preferably at least about 50%, still more preferably at least about 70%, and even more preferably at least about 90%.

B. Means of Practicing the Method

The present invention can be practiced by any suitable means. For example, the method herein can be practiced in batch, semi-batch, or continuous mode.

C. Corn-based food Products Having Reduced Levels of Acrylamide

Corn-based food products prepared according to the method herein can have a reduction in the acrylamide level of at least about 10%, preferably at least about 30%, more preferably at least about 50%, still more preferably at least about 70%, and even more preferably at least about 90%.

The method herein can be applied to the production of any suitable corn-based food product, including but not limited to carbohydrate-containing corn-based foods, especially low-moisture corn-based foods (e.g., less than about 10% moisture) that are heated during preparation. For instance, the method can be used to reduce the level of acrylamide found in fabricated snack foods, breakfast cereals, breads, cookies, crackers, toaster pastries, pizza crust, pretzels, corn tortillas, taco shells, grits, hominy, mush, hush puppies, popcorn, popcorn products, corn dogs, flours, doughs, starches, mixes, batters, beverages (e.g., alcoholic beverages such as whiskey), pie fillings, soups, gravies, stews, chilis, animal foods (e.g., dog food, cat food, ferret food, guinea pig food, rabbit food, rat food, mouse food, chicken food, turkey food, pig food, horse food, goat food, sheep food, monkey food, fish food), and any other food product comprising corn.

In one embodiment, tortilla chips have less than about 75 ppb acrylamide, preferably less than about 50 ppb, and more preferably less than about 10 ppb.

In another embodiment, corn chips have less than about 75 ppb acrylamide, preferably less than about 50 ppb, and more preferably less than about 10 ppb.

In yet another embodiment, a corn-based breakfast cereal, preferably corn flakes, has less than about 60 ppb acrylamide, preferably less than about 40 ppb acrylamide, more preferably less than about 20 ppb acrylamide, and most preferably less than about 10 ppb acrylamide.

In a preferred embodiment, tortilla chips are made from treated dried masa flour. In a preferred embodiment, the dried masa flour is rehydrated with water to form a masa dough that is then used to produce tortilla chips as described in WO 01/91581, published Dec. 6, 2001, by Zimmerman et al.

Although the method herein will generally be described in terms of preferred corn-based food products, it should be understood by one skilled in the art that the method herein can be applied to any suitable corn-based food product.

1. Dry-Milled Corn-Based Food Materials

The method herein can be used to make dry-milled corn products. The types of products produced by dry milling can include, but are not limited to, corn grits, corn meals, and corn flours. These dry milled products can be used in the making of food products such as breakfast cereals, mixes (e.g., pancake, cookie, muffin), baked goods, snack foods, coatings (e.g., breading or batters), anti-stick agents for bread loaves or pizzas, and baby foods.

In typical dry milling operations, the corn kernels are cleaned then degermed using techniques that are well known in the art. The dried corn is then milled to form a dry milled corn product. According to the present invention, enzyme can be added to the corn either before, during, or after milling, or combinations thereof.

For instance, enzyme can be added during the washing step prior to dry milling where the amount of water and length of contact time are both increased to allow for sufficient enzymatic reaction time. In one embodiment, enzyme is added to hydrated corn under elevated pressure and/or elevated temperature (e.g., at a pressure and temperature at which the enzyme is not deactivated or denatured). Any suitable water to corn ratio can be used, as one skilled in the art can readily determine. The length of time that the corn kernels are in contact with the water should be sufficient for the water to transport through the pericarp to the soft endosperm at the interior kernel. Preferably, the length of time the corn is in contact with the water is such that excessive swelling of the kernel does not occur. Ideally, the corn starch granules within the kernel will retain the characteristic of being birefringent when viewed under polarized light with a microscope. Any suitable water to corn contact time can be used, as one skilled in the art can readily determine, to achieve the desired level of asparagine reduction. The temperature of the water can be slightly elevated to enable a more rapid diffusion of the water through the pericarp. Preferably, the temperature is such that the corn starch granules remain birefringent (not gelatinized). Preferably, the water and corn kernel mixture is agitated.

The corn is then preferably dried prior to degerming. The corn can be dried by a number of means including, but not limited to, conductive, convective air, or radiant heat transfer modes as used with ovens, fluidized beds, drying towers, or packed bed unit operations. The drying conditions are preferably set to provide corn kernels comprising from about 1% to about 50% moisture, preferably from about 5% to about 35% moisture, more preferably from about 10% to about 30% moisture, and most preferably from about 15% to about 25% moisture. Next, the corn is dry milled. The corn can be dried and milled using techniques known in the art, such as those found in *Corn Chemistry and Technology*, Watson, S. A. and Ramstad, P. E., AACC Monograph Series, 1987 (hereinafter "*Corn Chemistry and Technology*"), pp. 351-376.

In another embodiment, corn kernels are degermed, then soaked in an aqueous enzyme solution.

In yet another embodiment, corn that is enzyme-treated during washing is used to make a dry-milled product, then the dry-milled product is again treated with enzyme. The total mixture is preferably agitated. Suitable mixing processes would include, but not be limited to batch holding tanks with impeller type agitators, continuous stirred type tank reactors, plug flow mixer reactors, fluidized bed mixers that use a dispersed gas phase as the means of providing movement, or extruder type mixers that can be single or multiple screw configurations. The level of mixing and agitation can be varied to improve the contact between the enzyme and the corn to reduce the amount of contact time needed while also maintaining other desirable properties of the corn product. The dry milled corn product would then be dried. Suitable drying process can include, but not be limited to drum drying, spray drying, spray cooling, fluidized bed ovens or towers or jet zone type dryers such as those known in the art.

A preferred embodiment of the present development comprises the use of the treated dry milled product directly in its wet state for making an end use product; this avoids the extra step and energy consumed by drying this material. The wet treated material can be used as an admixture with other dry raw material components to form a partially or completely hydrated dough composition that can optionally receive more added water.

In another embodiment, enzyme powder is added to the ground dried corn product. Instructions are included on the package of this dried corn product which instruct the user of the product to add an appropriate amount of water to the product, such that the enzyme converts the asparagine to aspartic acid during processing into a food product. Furthermore, the producers of this corn mill product with dry enzyme can provide instructions specifying appropriate temperature, water, pH, and incubation time such that the desired level of reduction can be achieved.

In another embodiment, the enzyme is added during the processing or the making of the finished product such as a breakfast cereal or snack. Enzyme treatment may occur during any production step in the making of a finished product, including but not limited to mixing the milled corn product with water or other wet ingredients, extruding, milling, or sheeting a dough comprising the milled corn product and optionally other ingredients. The enzyme may be added to the milled corn product in any feasible way, including but not limited to adding the enzyme to water or another liquid that is then mixed with the milled corn product, adding enzyme to the milled corn product prior to or during mixing with other dry or wet ingredients, injecting an enzyme solution during extrusion of the milled corn product, spraying, wiping or dripping an enzyme solution onto the milled corn product following mixing, extrusion, or sheeting by milling. Treating the milled corn during processing of the end-use product is preferable, as it avoids an added drying step if the dry milled corn product is enzyme treated separately prior to making the end use product.

In another embodiment, the treated material is admixed with other ingredients that have been previously hydrated to form a granular, agglomerated particulate or dough consistency.

In yet another embodiment, the dry milled corn product is treated with enzyme simultaneously with other raw materials comprising the final food product. The dry materials can be first blended as a separate, homogenous dry mixture or be compounded during mixing with the water and enzyme mixture.

2. Wet-Milled Corn-Based Food Materials

The preferred method for treating corn with enzyme for wet milling operations is the addition of enzyme to the inherent soaking, cooking, or steeping processes. Utilizing this existing step avoids introducing additional process complexity. The intent of these water contacting processes is to soften the corn kernel to enable increased diffusion of treatment chemicals, separation of the corn kernel components or size reduction through grinding. The water contacting process should be kept at conditions that would normally be used to deliver the desired corn product attributes provided the temperature is kept below a level that would be deleterious to the stability of the enzyme. These conditions typically include ratio of water to corn, contact time, pressure, and temperature. To ensure the functionality of the enzyme, preferably any ingredients that could affect the efficacy of the enzyme (e.g., components that alter pH) are added after the enzyme incubation period.

In one embodiment, the steeping of corn for starch production preferably has a volume of water from about 1.2 to 1.4 m³ per 2000 pounds of corn kernels. Preferably, the corn is steeped from about 22 to about 50 hours to enable the pericarp and endosperm to soften and allow the corn to increase in moisture content from about 16 to about 45% during the steeping process. The steeping water is preferably heated to a temperature from about 85° F. to about 150° F., more preferably from about 100° F. to about 135° F., and most preferably from about 120° F. to about 130° F. Processing aides such as sulfur dioxide can be optionally added to the water to enable more rapid diffusion of the water into the kernel matrix by assisting in the breakdown of the protein starch matrix. The steeping can be done by a batch or preferably a continuous process. Typically the process involves a series of steep tanks where steep water is countercurrently flowed from one tank to another. Processes for wet milling corn can be found in *Corn Chemistry and Technology*, at pp. 377-397.

A specialized wet milling process involves the production of masa, which is ground lime-cooked corn with a distinctive texture and flavor, as known in the art. See, e.g., *Corn Chemistry and Technology*, p. 410-411. Corn treated in this manner is most often used to make products such as tortilla chips, tortillas, and corn chips. The masa can be processed to directly make corn-based food products like tortilla chips or it can be ground and dried to make a masa flour to be used for later processing.

The process to make masa involves cooking whole kernel corn in the presence of a lime-water solution followed by steeping without added heat. The softened, lime treated corn is then washed with water, de-watered, then ground to a desired granulation. There are several outlets for the masa. It can be fed directly to a forming extruder to make snack products or sent to a sheet forming system followed by cooking (e.g., baking, grilling) to make traditional tortillas. In addition, tortilla chips can be prepared by frying the finished tortillas or a masa dough directly. Optionally, the masa can be dried and sifted to make a masa flour.

The enzyme can be added at multiple processing steps in the masa or food product making process. Preferably, treatment will occur early in the masa making process to allow sufficient residence time for completion of the enzymatic conversion of asparagine and before the drying step in the masa flour making process, or before the cooking step in making tortillas or masa-based snack foods, because a certain level of acrylamide may be formed in this drying step. Preferably, the enzyme treatment occurs before pH adjustment (e.g., the addition of lime), allowing for maximum efficacy of asparagine reduction.

In one embodiment of the masa making process, corn is processed into masa or masa flour using a traditional batch cooking and steeping process. The amount of water used to cook and steep the corn can be expressed as a dimensionless weight ratio of the weight of the water to the weight of corn. Preferably this ratio is from about 0.6 to about 3.0, more preferably from about 1.0 to about 2.0, much more preferably from about 1.0 to about 1.5, and most preferably from about 1.2 to about 1.5. Lime can be added to the water at any time, either before of during the cooking process to achieve the desired end product characteristic. In the traditional process, the lime is preferably added to the cooking water before the corn to maximize the contact time between the corn and lime-water solution.

Preferably in the present method, the lime is added to corn that has been pre-treated with enzyme. In one embodiment, the lime is calcium hydroxide in either its hydrous or anhydrous form. The amount of lime added to the water can be expressed as a dimensionless weight ratio of the weight of the lime to the weight of the corn. The weight ratio of lime to corn is preferably from about 0.01 to about 5.0, more preferably from about 0.10 to about 2.0, much more preferably from about 0.20 to about 1.0, and most preferably from about 0.20 to about 0.75. The cook time is preferably from about 1 to about 120 minutes, more preferably from about 4 to about 60 minutes, much more preferably from about 4 to about 45 minutes, and most preferably from about 20 to about 45 minutes. The temperature of the cooking water is preferably from about 130° F. to about 212° F., more preferably from about 150° F. to about 200° F., and most preferably from about 160° F. to about 195° F. The amount of time that the corn steeps or soaks in the lime-water after cooking is preferably from about 0.1 to about 48 hours, more preferably from about 2 to about 24 hours, much more preferably from about 2 to about 16 hours, and most preferably from about 4 to about 12 hours. The lime-water is allowed to cool without added heat during the steeping process. Alternate methods for making masa can include, but are not limited to, cooking in water without lime then adding lime during the steeping operation, changing the water after the cooking step to fresh water without lime, or changing the water after cooking to a new lime-water solution. The use of lime-water may not be compatible with the added enzyme, especially if the pH is very high, e.g. greater 10. In situations where the pH is high, it is preferred that enzyme is added before or after the lime-water treatment. However, enzyme can be used at any suitable point in the masa process.

One embodiment of the masa process is the traditional masa making process, which comprises the following steps:
(1) Combining corn with water and lime to form a mixture;
(2) Cooking the mixture;
(3) Steeping the mixture to form nixtamal;
(4) Optionally washing and/or or neutralizing the nixtamal, preferably with acid solution;
(5) Grinding the nixtamal to form masa;
(6) Optionally mixing the masa with other ingredients;
(7) Optionally conveying the masa to processing equipment such as an extruder or sheeter-cutter;
(8) Optionally subjecting the masa to a fabrication process such as extruding, sheeting, cutting, or combinations thereof.
(9) Cooking the masa, preferably by baking and/or frying, to form the finished food product; and
(10) Adding enzyme before, during and/or after any of steps 1-8 above.

For the process of making masa flour, the following steps may be used after grinding the nixtamal into masa dough. Either un-pretreated or pretreated masa can be processed by the following steps. In general, the method comprises:
(1) Drying the masa;
(2) Optionally sifting the masa; and
(3) Optionally adding enzyme to the masa.

In one embodiment, pretreated masa is further treated with enzyme to achieve greater asparagine, and thus acrylamide, reduction.

Also, alternate means of masa and masa flour production may be used, including but not limited to extrusion with or without lime as described in U.S. Pat. Nos. 5,558,886 and 4,985,269, continuous cook-steep processes, continuous production using separate components of cereal grain as described in U.S. Pat. No. 6,068,873, or other methods known to those skilled in the art. Enzyme treatment to reduce asparagine may occur during any suitable step of the process described above or any suitable step of any alternate processes, and optionally during multiple steps or with multiple treatments. Methods of adding the enzyme to the corn product for treatment include, but are not limited to, adding dry enzyme to the corn, adding enzyme to the cook water before, during or after cooking, adding enzyme before, during or after steeping, adding enzyme before, during or after washing, adding enzyme during a wash step optionally allowing the corn to soak in the enzyme solution, adding dry enzyme or optionally in aqueous solution before or during grinding, adding dry or aqueous enzyme during mixing, adding dry or aqueous enzyme during extrusion or sheeting, or spraying, wiping or dripping an aqueous enzyme solution onto the dough before, during or after grinding, mixing, extruding, or sheeting. These alternate methods for treating corn during the masa making process need not impact the effectiveness of reducing asparagine content provided a sufficient residence time is maintained with an asparagine reducing enzyme at a temperature that will not significantly degrade the enzyme. Optimum conditions can be obtained from the manufacturer of the specific enzyme, or one skilled in the art can readily determine appropriate conditions for enzyme treatment.

An optional method of enzyme treatment of dry masa flour is adding enzyme to the masa flour as a dry powder. For example, when added as a dry powder, the end-user can add the water that allows the enzyme to convert the asparagine to aspartic acid during processing of the masa flour into a finished food product. The enzyme can be optionally removed or inactivated. The water can optionally be removed after the incubation period. The producers of this masa flour with dry enzyme can provide instructions specifying appropriate temperature, water, pH, and incubation time such that the desired level of reduction can be achieved.

Masa flour and pre-gelatinized or pre-cooked corn flours can alternatively be made with an extrusion type process where the corn is conveyed by single or multiple screws through a tight tolerance enclosure such as a barrel or shaft. It is important to maintain the temperature of the extrudate to avoid degrading the enzyme composition. Preferably, the enzyme system would be introduced into the first zones of the extruder where the temperature and residence time would be set to favor maximum activity of the enzyme. More preferably, two extruders are used in series where the first extruder serves as a mixer for introduction of the enzyme system to enable thorough contacting with the corn under conditions favorable to maximizing the enzymatic conversion. Most preferably, the corn is pre-conditioned with the enzyme system in a pre-mixer prior to introduction to the extrusion process. The mix system can include, but is not limited to, a batch tank, series of tanks, plug flow reactor, sigmoid mixer, ribbon or paddle blenders, planetary mixer, comminutive mixers, fluidized bed, or spray cooling operation or combinations thereof.

Correspondingly, the corn used for wet milling operations can first be enzyme pre-treated to obtain a low asparagine level, then forwarded in a wet state for continued processing or alternately dried and saved for later use.

Alternately, the final products from corn wet milling operations including but not limited to hominy, grits, nixtamal, masa, and starches can be enzyme treated post wet milling production.

3. Corn-Based Foods Made from Dehydrated Corn Products

The dehydrated corn products can be used as is, or can optionally be rehydrated and used to produce corn-based food products such as polenta, mush, corn bread, corn muffins, tortillas, grits and other corn snacks such as corn chips and extruded corn puffs. The dehydrated corn products can also be used in breads, gravies, sauces, baby food, or any other suitable corn-based food product. In one embodiment, the corn-based food product is used as a coating for fried foods, such as fish, zucchini, mushrooms, and cheese sticks. In another embodiment, the product is used as a release agent, for example sprinkled on the bottom of a pizza or on a pizza pan to facilitate release of the pizza from the pan. The product can also be used as a release agent for loaves of bread.

The enzyme-treated dehydrated corn product can be used to make fabricated corn snacks, preferably tortilla chips or corn chips. In preferred embodiments, additional enzyme is used during the snack fabrication process (in addition to that enzyme used in making the dehydrated corn product) in order to further increase the level of acrylamide reduction.

In one embodiment, a fabricated corn snack is made by the method comprising:
   (1) adding an asparagine-reducing enzyme to a corn-based dough comprising corn masa;
   (2) forming a snack piece from the dough; and
   (3) cooking the snack piece to form a fabricated snack.

In another embodiment, a fabricated snack is made by the method comprising:
   (1) blending dry ingredients comprising masa flour and optionally other ingredients;
   (2) adding water;
   (3) forming a dough;
   (4) optionally forming a dough sheet;
   (5) forming a snack piece; and
   (6) cooking the snack piece to form a fabricated snack;
   (7) adding an asparagine-reducing enzyme before, during, or after any of steps (1)-(5) above.

In one embodiment of the invention, a tortilla chip made from masa is made by the method comprising:
   (1) adding enzyme to a dough comprising masa and optionally other ingredients;
   (2) forming a snack piece from the dough; and
   (3) cooking the snack piece to form a tortilla chip.

In another embodiment, a tortilla chip made from masa flour is made by the method comprising:
   (1) blending dry ingredients, comprising masa flour and optionally other ingredients;
   (2) optionally adding emulsifier to dry ingredients;
   (3) adding water;
   (4) mixing to form a dough;
   (5) forming a dough sheet;
   (6) forming a snack piece from the dough sheet;
   (7) cooking the snack piece to form a fabricated snack; and
   (8) adding an asparagine-reducing enzyme before, during, or after any of steps (1)-(6) above.

Enzyme can be added at any suitable stage of the process, for instance enzyme may be added during the blending, optionally adding emulsifier, adding water, mixing, and/or forming steps. Alternatively, the enzyme can be applied, preferably as a solution, to the dough surface; this can occur either before or after the snack pieces are formed from the dough sheet. In one embodiment, the enzyme solution is added to the surface of the dough sheet.

Cooking can be performed by any suitable method, for instance by frying, baking, or a combination of frying or baking. Furthermore, the forming and cooking steps can be carried out simultaneously, such as by extrusion.

In one embodiment, tortilla chips have less than about 75 ppb acrylamide, preferably less than about 50 ppb, and more preferably less than about 10 ppb.

In another embodiment, corn chips have less than about 75 ppb acrylamide, preferably less than about 50 ppb, and more preferably less than about 10 ppb.

D. Article of Commerce

Another embodiment of the invention is an article of commerce comprising:

(a) a corn-based food product, wherein said corn-based food product has a reduced level of acrylamide;

(b) a container for containing the corn-based food product; and (c) a message associated with the container.

The message informs the user that the corn-based food product contains a reduced level of acrylamide. The message can be printed material attached directly or indirectly to the container, attached directly or indirectly near the container, or alternatively can be a printed, electronic, or broadcast message associated with the corn-based food product or with the container.

In one embodiment of the present invention, a corn-based food product having reduced levels of acrylamide is provided in a container having a message associated therewith. Any container from which the corn-based food product can be dispensed, presented, displayed, or stored is suitable. Suitable containers include, but are not limited to, bags, canisters, boxes, bowls, plates, tubs, and cans.

The message informs the consumer that the corn-based food product contains a reduced level of acrylamide. The message can be printed material attached directly or indirectly to the container, attached directly or indirectly near the container, or alternatively can be a printed, electronic, or broadcast message associated with the corn-based food product or with the container. Suitable messages include, but are not limited to, messages that communicate "reduced" or "low" levels of acrylamide, messages that communicate that less than a specified amount of acrylamide is present (e.g., less than 5 ppb), and messages that communicate that the corn-based food product meets or exceeds a suggested or mandatory level (e.g., regulatory threshold or signal level).

In another embodiment, the message informs the consumer that the corn-based food product is made with an ingredient or ingredients with reduced or low levels of asparagine.

Analytical Methods

Parameters used to characterize elements of the present invention are quantified by particular analytical methods. These methods are described in detail as follows.

1. Acrylamide

Method for Measuring Acrylamide (AA) in Food Products

Summary

Food products are spiked with 1-$^{13}$C-acrylamide ($^{13}$C-AA) and extracted with hot water. The aqueous supernatant is extracted three times with ethyl acetate, and the ethyl acetate extracts are combined and concentrated and analyzed by LC/MS with selected ion monitoring for specific detection of AA and $^{13}$C-AA.

Extraction of Sample

1. Weigh 6.00±0.01 g of sample into a 125-mL Erlenmeyer flask. Note: Place the sample into a food processor and pulse for 30 seconds so that the particle size is about ⅛ inch or less. If the sample is too small to be effectively ground in a food processor, place the sample in a new plastic bag (e.g., Whirl-Pak™ or equivalent) and pulverize with a rubber mallet until the particle size is ⅛ inch or less.

2. Add 120 μL of 100 ng/μL $^{13}$C-AA in de-ionized distilled water (ISTD 2), with an adjustable 1000-μL pipette (calibrated), directly onto the sample.

3. Using a dispenser, add 40 mL of de-ionized distilled water to the flask and cover with foil.

4. Place into a 65° C. water bath for 30 min.

5. With a dispenser, add 10 mL of ethylene dichloride to the flask, and homogenize with a Tekmar Tissumizer™ (SDT-1810) or Ultra-Turrax® (T18 Basic) for 30 seconds, or until uniform. Rinse the probe into the flask with deionized distilled water.

6. Place 25 g of the homogenate into an 8-dram vial

7. Tightly cap the tube and centrifuge for 30 minutes at 2500-5200 RPM.

8. Transfer 8 g of supernatant to another 8-dram vial being careful to avoid solid particles.

9. Add 10 mL of ethyl acetate with a dispenser, cap, and vortex for 10 seconds.

10. Allow any emulsion to break up; help by swirling or shaking once or twice and then allowing layers to split.

11. Transfer as much of the top layer (ethyl acetate) as possible to a scintillation vial, without transferring any liquid (water) from the interface. Extract twice more with 5-mL portions of ethyl acetate and add to the same scintillation vial. Then, add approximately 2 g of anhydrous sodium sulfate.

12. Concentrate the extract with a gentle stream of nitrogen in a 60-65° C. water bath to about 1 mL. Transfer the extract to a Pierce REACTI-VIAL™ or equivalent conical-shaped glass vial and further concentrate the extract to a final volume of approximately 100-200 μL. Place this extract into an autosampler vial with a conical sleeve.

Preparation of Standards

| | Stock Solutions and Internal Standards | | | |
|---|---|---|---|---|
| Solution | Weight | Volumetric Flask | Solvent | Concentration (ppm) |
| Stock 1 | 0.1000 g Acrylamide (AA) | 100-mL | Ethyl Acetate | 1000 |
| ISTD 1 | 0.0100 g $^{13}$C-Acrylamide | 100-mL | Ethyl Acetate | 100 |
| Stock 2 | 0.1000 g Acrylamide (AA) | 100-mL | Deionized Distilled Water | 1000 |
| ISTD 2 | 0.0100 g | 100-mL | Deionized | 100 |

-continued

| | $^{13}$C-Acrylamide | | Distilled Water | |

Intermediate Standards

| Solution | Volume Stock 1 AA (μL) | Volumetric Flask (mL) | Solvent | Concentration (ppm) |
|---|---|---|---|---|
| INT 1 | 100 | 10 | Ethyl Acetate | 10 |
| INT 2 | 1000 | 10 | Ethyl Acetate | 100 |

Calibration Standards

| Standard | Volume INT 1 (μL) | Volume INT 2 (μL) | Volume ISTD 1 (μL) | Volumetric Flask (mL) | Solvent | Conc. AA (ppm) | Conc. ISTD 1 (ppm) |
|---|---|---|---|---|---|---|---|
| 0 | 0 | 0 | 450 | 10 | Ethyl Acetate | 0 | 4.50 |
| 0.25 | 250 | 0 | 450 | 10 | Ethyl Acetate | 0.250 | 4.50 |
| 0.75 | 750 | 0 | 450 | 10 | Ethyl Acetate | 0.750 | 4.50 |
| 1.5 | 0 | 150 | 450 | 10 | Ethyl Acetate | 1.50 | 4.50 |
| 3.0 | 0 | 300 | 450 | 10 | Ethyl Acetate | 3.00 | 4.50 |
| 5.0 | 0 | 500 | 450 | 10 | Ethyl Acetate | 5.00 | 4.50 |

Homogenizer Cleaning Procedure

Use this cleaning procedure between every sample.
1. Fill a 1-L Erlenmeyer flask with hot tap water (≈80% full) and add a drop of Dawn™ dishwashing liquid (available from the Procter & Gamble Co.) or equivalent.
2. Insert the dispersing element probe into the water as far as possible.
3. Homogenize the solution for about 10-1 5 seconds.
4. Empty the cleaning solution from the Erlenmeyer; rinse and refill the flask with hot tap water.
5. Homogenize again for about 10-15 seconds.
6. Empty the flask and refill with hot tap water; homogenize again for about 10-15 seconds.
7. If the water is not clear and free of particulates, continue homogenizing clean hot tap water as many times as necessary to achieve this condition.
8. When the hot tap water is clear and free of particulates, rinse the probe with deionized distilled water.

Analysis by LC/MS

Samples are analyzed using a Waters 2690 LC interfaced to a Micromass LCZ mass spectrometer.

| Mobile Phase | 100% H$_2$O, 10 mM NH$_4$Ac, adjusted to pH 4.6 w/formic acid |
| Column | 2.0 mm × 150 mm, YMC C18 AQ (available from Waters Corp.) |
| Flow rate | 0.2 mL/min |
| Interface | Direct (no split) |
| Injection volume | 5 μL |
| MS ionization mode | Electrospray, positive ion mode |
| MS detection mode | Selected ion monitoring: m/z 72 (AA), m/z 73 ($^{13}$C-AA); dwell times: 0.5 s |

Data Analysis

Response ratios (area of AA peak/area of $^{13}$C-AA peak) are plotted against the corresponding concentration ratios for a series of five standards in ethyl acetate. All standards contain 4.5 pg/mL $^{13}$C-AA, and AA concentrations ranging from 0 to 5 μg/mL. Linear regression results in a calibration curve from which concentration ratios in extracts are determined from measured response ratios. When this concentration ratio is multiplied by the accurately known $^{13}$C-AA level (nominally 2 ppm) added to sample in step two of the extraction procedure, the level of AA in ppm results.

Sample Calculation for LC/MS:

The calibration curve is generated by plotting the response ratio (area m/z 72/area m/z 73) on the y axis vs. the concentration ratio ([AA]/[13C-AA]) on the x-axis. For this example, the equation of that line is y=0.899x+0.0123.

Measured area of AA peak (m/z 72) at 4.0 min: 100,000

Measured area of 13C-AA peak (m/z 73) at 4.0 min: 500,000

Response ratio $R_r$=0.200. From the slope and intercept of the calibration curve, the concentration ratio $R_c$ is calculated: $R_c$=(0.200−0.0123)/0.899=0.209

Given the spike level of 13C-AA in the sample (2 ppm), the measured level of AA is 0.209×2 ppm=0.418 ppm Quality Assurance/Quality Control (QA/QC)
1. All balances used in the preparation of standards and/or samples, must have their calibrations checked weekly with a set of qualified weights. The balances should be checked with at least three weights covering the range of sample/standard weights to be measured.
2. A six-point calibration curve should be performed daily.
3. A working reference material (WRM) should be analyzed with each set of samples. The concentration of this material should be within 2 σ of the running mean. If it is not, the instrument should be recalibrated and the WRM recalculated.

2. Asparagine

Determination of Asparagine and Aspartic Acid in Food and Beverage Products

Principle

A weighed amount of sample is mixed with 5% HCl and heated for 30 minutes, then homogenized. A portion of the homogenate is centrifuged and then a portion of the supernatant is diluted and treated with FMOC reagent (9-fluorenyl-methyl chloroformate), which reacts with asparagine and aspartic acid to form a highly fluorescent derivative. Reverse-phase HPLC is then used to resolve FMOC-asparagine from other sample matrix components. Detection is by fluorescence emission at 313 nanometers (nm) upon excitation at 260 nm. Analysis of standards of known concentration permits quantification.

Linearity

Working calibration curve of four standards (50-600 ppm) give a correlation of 0.998 or better. A curve taken out to 2000ppm also gives a correlation of 0.998.

Accuracy

Potato Products:

Potato starch is spiked with four levels of both asparagine and aspartic acid (40, 200, 400, and 600 ppm). Recovery of asparagine is 100% (Relative standard deviation of less than 4%) and recovery of aspartic acid is 110% (Relative standard deviation of less than 4%).

REFERENCES

1. Herbert, P.; Santos, L; Alves, A. Journal of Food Science (2001), 66(9), 1319-1325.
2. Heems, Dany; Luck, Geneviewe; Fraudeau, Chrisophe; Verette, Eric. Journal of Chromatography, A (1998), 798 (1+2), 9-17.

System Repeatability

A working reference material of potato chip is run in duplicate over five days. Results are as follows:

|  | ug/g asparagine | ug/g aspartic acid |
|---|---|---|
| ave | 7832.07 | 1440.98 |
| STD | 625.59 | 195.80 |
| % RSTD | 7.99 | 13.59 |

Below Are Suggested Chemicals and Equipment; However, Substitutions of Equivalent Materials Are Acceptable.

| CHEMICALS | |
|---|---|
| Water, HPLC or | |
| Milli-Q ™ Grade (Millipore) | |
| Acetonitrile, HPLC Grade | Burdick & Jackson #AH015-4 |
| Methanol, HPLC Grade | Fisher #A452-4 |
| Ethyl Acetate | Baker #9280-3 |
| Pentane | Burdick & Jackson #GC312-4 |
| Asparagine monohydrate | EM Science |
| Aspartic acid | Sigma #A-8949 |
| aminoisobutyric acid | Sigma #A-8379 |

| CHEMICALS | |
|---|---|
| Water, HPLC or | |
| Milli-Q ™ Grade (Millipore) | |
| 9-Fluorenyl Chloroformate (FMOC) | ICN #150200 |
| Sodium Borate | EM Science #SX 0355-1 |
| Boric Acid | Fisher #A-73 |
| Sodium Bicarbonate | ICN #194847 |
| Tetramethyl Ammonium Chloride | Fisher #04640-500 |
| Sodium Citrate | MCB #SX445 |
| Citric Acid anhydrous | Baker #0122-01 |
| Acetone | Burdick & Jackson #010-4 |
| Hydrochloric Acid, 0.1 N | Fisher #SA48-500 |
| Calcium Chloride Dihydrate | Aldrich #22,350-6 |

Equipment

Transfer Pipettes, polyethylene (Samco #222)
Volumetric Flasks (25, 100, 250, 1000 ml)
Volumetric Pipet (10 ml)
Graduated Cylinders (100-1000 ml)
HPLC reservoirs (500 ml, 1 or 2 liter)
Beakers
Magnetic stirrers/stir bars
Analytical (4-place) balance
Scintillation Vials
Centrifuge tubes, screw cap (100×16 mm) with caps
Autosampler vials (8×30 mm, 1 ml), with crimp caps Safety: This method requires the use of a fume hood, and involves exposure to chemicals. Please review Safe Practices for Fume Hood Use and Chemical Spills.

| INSTRUMENT | MODEL | MANUFACTURER |
|---|---|---|
| Robot | Microlab ® SPE | Hamilton |
| Pump/HPLC injector | HP 1100 | Agilent |
| Detector | RF10AXL | Shimadzu |
| Data System | Chemstation | Agilent |

Column

Phenomenex Luna 100×4.6 mm C-18(2) 3 micron # 00D-4251-EO

Preparation of Reagents

Diluent (pH 8.3-8.5; 100 ml).

1. Weigh 3.0 grams of Sodium Borate, 3.0 grams of Boric Acid, and 8.0 grams of Sodium Bicarbonate into a dry tared beaker.
2. Place an empty 800 ml beaker on a magnetic stirrer. Add about 500 ml of Milli-Q™ water and a stir bar. Stir the water vigorously without splashing.
3. Quantitatively transfer the reagents from step I to the water; stir until they are completely dissolved.
4. Quantitatively transfer the solution from step 3 to a 1-liter volumetric flask and dilute to volume with Milli-Q™ water; mix well. Stable for up to six (6) months.

Calcium Chloride Solution (100 grams).

1. Weigh 40 grams of Calcium Chloride Dihydrate into a tared 250 ml beaker.
2. Add 60 grams of Milli-Q™ water. Mix well. Store at ambient conditions in a capped glass bottle. Stable for up to 1 year.

Extraction Solvent (Pentane: Ethyl Acetate 80:20; 500 ml)

Safety: pentane and ethyl acetate are volatile and flammable. Perform the following operations in a Fume Hood.
1. Transfer 400 ml of pentane to a 500 ml HPLC reservoir bottle.
2. Add 100 ml ethyl acetate. Mix well. Store capped in/under the Fume Hood.

Mobile Phase (Buffer:Methanol:Acetonitrile 60:5:35,pH 3.2, 2 L)
1. Weigh 1.35 grams of Tetramethyl Ammonium Chloride, 3.65 grams of Citric Acid, and 1.60 grams of Sodium Citrate into a dry tared beaker.
2. Place an empty 800 ml beaker on a magnetic stirrer. Add about 500 ml of Milli-Q™ water and a stir bar. Stir the water vigorously without splashing.
3. Quantitatively transfer the reagents from step 1 to the water; stir until they are completely dissolved.
4. Quantitatively transfer the solution from step 3 to a 1 liter graduated cylinder and dilute to 1000 ml with Milli-Q™ water; mix well.
5. Transfer to a 2-liter HPLC mobile phase reservoir.
6. Add 200 ml Milli-Q™ water, 100 ml methanol and 700 ml acetonitrile. Add the latter two solvents slowly with vigorous stirring. Perform this operation in a hood, and wear personal protective equipment. Refer to the relevant Material Safety Data Sheets (MSDS) for specific details.
7. Degas the mobile phase by vacuum aspiration while stirring.

FMOC Reagent Solution (in Acetone)
1. Weigh 0.10 grams of FMOC reagent into a tared 100 ml volumetric flask.
2. Add acetone to dissolve and dilute to volume with same. Mix well. Perform this operation in a hood. Wear PPE specified in the MSDS for the chemicals.
3. Store refrigerated for no more than six (6) months.

Acid Solution for Sample Extraction (5% HCl)
1. Add 100 ml of Milli-Q™ water into a 200 ml volumetric.
2. Add 4 ml of IN HCl to volumetric.

Bring to volume with Milli-Q™ water.

Preparation of Internal Standard (Aminoisobutyric Acid)

ISDT A—Internal Standard Stock A
1. Weigh 0.5 grams of aminoisobutyric acid into a tared 250 ml volumetric
2. Add 25 ml of 1.0N HCl and about 100 ml Milli-Q™ water. Mix by swirling until dissolved. Dilute to volume with Milli-Q™ water and mix well. Store refrigerated for no more than six (6) months.

ISTD B—Working Internal Standard Solution B (This Solution is Added to Calibration Standards)
1. Pipet 1 ml of Internal Standard Stock A into a 100 ml volumetric flask.
2. Dilute to volume with Milli-Q™ water. Stable for one month.

Preparation of Calibration Standard(s)

Stock Calibration Solution.

Into a tared 50 ml volumetric, weigh 0.100 g (+/−0.001 g) asparagine and 0.100 g (+/−0.001 g) aspartic acid. Add 25 mL Milli-Q™ water and 1 mL 1 N HCl. Place in sonic bath until dissolved, then bring to volume with Milli-Q™ H2O. Solution is good for 6 months refrigerated.

Working Standards.

Prepare the following working calibration standards:

| Std # | mL stock | final volume (mL) | ppm |
| --- | --- | --- | --- |
| 1 | 5 | 200 | 50 |
| 2 | 5 | 100 | 100 |
| 3 | 1 | 10 | 200 |
| 4 | 3 | 10 | 600 |

Solutions are good for one month refrigerated.

Preparation of Samples
1. Weigh 1 g of sample into 125 ml Erlenmeyer flask.
2. Add 48.0 ml of 5% HCl solution to each sample.
3. Add 2 ml ISTD A to each sample.
4. Cover each flask with aluminum foil and place in 60 C. water bath for 30 minutes.
5. Add 10 mL dicloroethane to each sample.
6. Homogenize sample for 60 seconds.
7. Pour portion of sample into 30 ml centrifuge tube.
8. Centrifuge at 10000 rpm for 32 minutes at 5° C. The supernatant is used in "Samples—Diluting" step 1.

Preparation of Standards and Samples

Three Microlab® methods are run in order to dilute the samples/standards, add the internal standard, and form the FMOC derivative. These are summarized below.

| Operation | Microlab method used |
| --- | --- |
| Dilution | TRANSDIL |
| Addition of Internal Standard | ADDISTD |
| Formation of FMOC derivative | ADDFMOC |

Preparation of Samples and Standards Using Microlab® Robot

Step 1: Standards—Adding ISTD and Dilution Step
1. Prepare two sets of tubes for each standard. Place approximately 2 mL of standard in one set of tubes, place these filled tubes on the left most position of the Microlab®.
2. Place the rack with empty tubes in the rightmost rack position of the Microlab®.
3. Fill a 20 ml glass (scintillation) vial with Working Internal Standard Solution B and place on the Microlab® workspace.
4. Select method ADDISTD. (Mixes 200 ul ISTD B, 50 ul standard solution, to 4000 ul total volume with Milli-Q™ water).
5. Execute the method.
6. Remove the tube set from the left position and set aside for discard.
7. Remove the Working Internal Standard Solution from the Microlab® work space and refrigerate.

Set aside right side tubes for step 3.

Step 2: Samples—Dilution Step (ISTD was Already Added During Sample Preparation)
1. Prepare two sets of tubes for each sample. Place approx. 2 mL of sample in one set of tubes, place these filled tubes on the left most position of the Microlab®.
2. Place the rack with the empty tubes in the rightmost rack position of the Microlab®.
3. Select method TRANSDIL. (Set # of samples, 50 ul for amount of sample, and 4000 ul for final dilution amount with Milli-Q™ water.)
4. Execute the method.
5. Remove the tube set from the left position and set aside for discard.

Set aside right side tubes for step 3.

Step 3: Addition of FMOC Reagent—Making Fluorescent Derivative
1. Prepare a rack of 100×16 mm screw-cap tubes.
2. Place the rack in the rightmost rack position of the Microlab®.
3. Place standard and sample tubes from above dilution steps in leftmost rack position of Microlab®.
4. Transfer an aliquot (22 mL) of FMOC reagent solution to a glass scintillation vial. Add approximately 100 µL of 40% Calcium Chloride solution; mix well. (Calcium chloride is added to make the FMOC reagent "charged"—necessary for detection by Microlab®).
5. Place the vial on the Microlab® workspace.
6. Select method ADDFMOC.
7. Switch syringes 1 & 2 from water to Diluent (pH 8.3-8.5).
8. Perform a wash of at least five (5) cycles for syringes 1 & 2 using Diluent (pH 8.3-8.5)
9. Execute method ADDFMOC. (Mixes 450 ul of FMOC solution, 250 ul sample from ADDISTD above to final volume of 1300 ul with diluent solution).
10. Remove the tube set from the SAMPLE rack position and set aside.
11. Remove the FMOC reagent solution from the Microlab® workspace and refrigerate.
13. Remove the tube set from the rightmost position and place in fume hood. Let stand for at least 10 minutes or until solution is clarified (but no longer than 20 minutes).
14. Add 2 ml of Extraction Solvent to each tube. Cap and vortex at high speed for two (2) minutes to extract unreacted FMOC reagent.
15. Prepare another tube set of 55×16 mm tubes. Add 1 ml of mobile phase solution to each tube.
16. Transfer the 1.0 mL of aqueous (lower) layer from the centrifuge tubes to the 55×16 mm tubes.
17. Discard the upper (organic) layer.
18. Transfer samples to autosampler vials and seal.

Chromatography

Operating Conditions

HP 1100 with Chem Station software

Detector: Waters 474 Scanning Fluorescence detector
  Mode: Norm
  Signal: 0.0000
  Wavelength: Ex 260Em 313
  Gain: 10
  Atten: 1
  Response: FST Column: Phenomex Luna C18 (2) 100×4.6 mm 3 u LC Method Flow: 1.000 ml/min
Isocratic run (see preparation of reagents—Mobile Phase)
Injection volume: 10.0 ul
Temperature settings: not controlled Calculations Sample solutions are calculated against a standard curve of known amounts using area counts:

$$y=mx+b$$

$$y(\text{ratio asparagine/ISTD})=m(\text{slope})\times(\text{asparagine concentration})+b(y\text{-intercept})$$

$$(y-b)/m=x$$

$$\text{ppm asparagine}=(\text{area asparagine/area ISTD}-\text{intercept})/\text{slope}$$

Example:

$$\text{ppm asparagine}=(215.45436/551.828--0.0165)/0.0023=176.93 \text{ ppm}$$

[ppm=ug/mL]

Correction for dilution/homogenization in sample preparation step.

$$\text{ug/g asparagine} = \text{ppm asparagine found} \times \frac{\text{mL sample dilution (50)}}{\text{grams of sample}}$$

$$[\text{ppm} = \text{ug/mL}]$$

Example:

$$\text{ug/g asparagine} = 176.93 \text{ ppm} \times \frac{50 \text{ mls}}{1.0083 \text{ g}} = 8773.65 \text{ ug/g}$$

Run Acceptability Criteria:
  the Check Sample of Working Reference Material accuracy must be within 10% of known result for asparagine.
  the linearity of the calibration curve ($r^2$) must be 0.995 or greater.

Sample Chromatogram of LC Analysis

Figure 3:
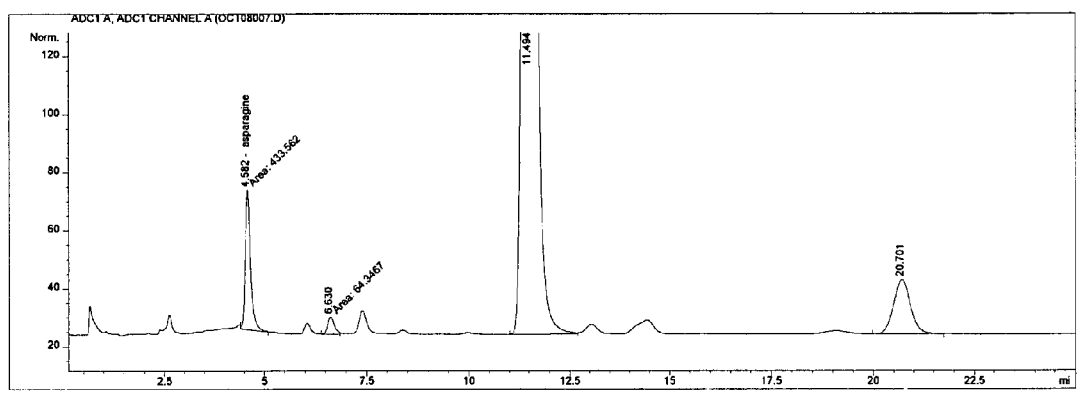
FIG. 3.

FIG. 3 sets forth a sample chromatogram of LC analysis.

| RT | Compound |
| --- | --- |
| 4.5 min | asparagine |
| 6.6 min | aspartic acid |
| 11.5 min | FMOC reagent |
| 20.7 min | ISTD |

3. % Reduction of Acrylamide

% Reduction Acrylamide=[(Acrylamide level in control sample−Acrylamide level in enzyme-treated sample) / Acrylamide level in control sample]×100.

The control sample is prepared in exactly the same manner as the enzyme-treated sample, with the exception that enzyme is not added.

4.% Reduction of Asparagine

% Reduction Asparagine=[(Asparagine level in control sample−Asparagine level in enzyme-treated sample)/Asparagine level in control sample]×100.

The control sample is prepared in exactly the same manner as the enzyme-treated sample, with the exception that enzyme is not added.

EXAMPLES

The following examples are illustrative of the present invention but are not meant to be limiting thereof.

Example 1

Dehydrated Dry-Milled Corn Product

Degermed white corn flour is prepared according to conventional methods. An effective amount of asparaginase is added before grinding. The resulting degermed white corn flour has greater than 10% reduction in acrylamide.

Example 2

Dehydrated Wet-Milled Corn Product

White corn masa flour is prepared according to conventional methods. An effective amount of asparaginase is added before drying. The resulting masa flour has greater than 10% reduction in acrylamide.

Example 3

Fabricated Tortilla Chips

Tortilla chips are made using the white corn masa flour of Example 2 using the method described in WO 01/91581, published Dec. 6, 2001, by Zirmmerman et al. The resulting tortilla chips have greater than 10% reduction in acrylamide.

Example 4

Article of Commerce

The tortilla chips of Example 3 are packaged in a bag for sale to consumers. Printed on the bag is a message stating, "Acrylamide-free product!"

Example 5

Article of Commerce

The tortilla chips of Example 3 are packaged in a bag for sale to consumers. Printed on the bag is a message stating, "Low in acrylamide!"

Example 6

Article of Commerce

The tortilla chips of Example 3 are packaged in a bag for sale to consumers. Printed on the bag is a message stating, "Acrylamide reduced by over 90%!" A television commercial for the chips communicates the message, "Our chips are lower in acrylamide!"

Example 7

Article of Commerce

Uniformly-shaped fabricated tortilla chips having less than 40 ppb acrylamide are packaged in a triangular canister for sale to consumers. A television commercial for the chips communicates the message, "Acrylamide-reduced!"

Example 8

Article of Commerce

The tortilla chips of Example 3 are placed in a wicker basket and served to restaurant patrons. A sign posted inside the restaurant where the corn chips are sold reads, "Our corn chips contain reduced levels of acrylamide!"

Example 9

Article of Commerce

The tortilla chips of Example 3 are packaged in a bag for sale to consumers. Printed on the bag is a message stating, "Made from ingredients low in asparagine!"

Example 10

Corn Flakes Breakfast Cereal

Yellow corn is broken (milled) so as to yield a No. 4 to No. 5 grit, free of germ and bran. These large pieces represent about ½ of a corn kernel; and they retain their identity throughout the processing, each particle eventually emerging a corn flake. Into a cylindrical pressure cooker is placed about 1700 lb. of the grits and 36 gal. of a flavoring syrup consisting of sugar, malt (nondiastic), salt, and water. An effective amount of asparaginase is added to the pressure cooker and the mixture is allowed to soak for several hours. Next, the mixture is cooked.

During the cooking period the charge accumulates additional water from the steam introduced into the retort, rising to about 33% moisture. Cooking is done in a slowly rotating retort at 15 to 23 (typically 18) psi steam pressure for 1-2 hr. Different lots of corn may vary considerably in the duration of the cooking time required. The end point can be judged by examining a small sample of the charge which is blown out through a gate valve for this purpose. A uniform translucency in the kernels indicates and adequate cook. At this time, the pressure is reduced to the atmospheric level, the retort is opened, and the contents are dumped out onto a moving belt.

After the lumps from the cooker are broken down to individual particles by a revolving reel, they are distributed to a set of driers. The latter devices are essentially large tubes or tanks extending vertically for several stories. The wet kernels enter the top and are dried by a countercurrent of hot (150° F.) air as they travel to the bottom.

The dried particles now contain 19-23% moisture, but this water is unevenly distributed, so the material is transferred to tempering bins for several hours (as many as 24) so that the moisture may equilibrate. After tempering, the hard, dark brown grits are ready for flaking.

The flaking rolls are steel cylinders weighing over a ton each, and revolving at a speed of about 180-200 rpm. Hydraulic controls maintain a pressure of over 40 tons at the point of contact of the rolls. The rolls are cooled by internal circulation of water. The cooked dried grits are pressed into thin flakes as they pass through the rolls. He product is still rather flexible at this time, lacking the desired crispness and preferred flavor of the finished corn flake.

From the rolls, the flakes pass directly to the rotating toasting ovens, which are usually gas fired. The moist flake is tumbled through the perforated drums and passes within a few inches of the gas flames. Treatment may be 50 sec at 575° F., or 2-3 min at 550° F. In addition to being thoroughly dehydrated by the process, the flakes are toasted and blistered. They emerge from the oven with less than 3% moisture.

From the ovens, the flakes are carried by belts to expansion bins where they are permitted to cool to room temperature. En route, the product is cooled by circulating air and is usually treated with a spray of a solution of thiamin and other B vitamins.

The resulting corn flakes have greater than 10% reduction in acrylamide.

Example 11

Article of Commerce

The corn flakes of Example 10 are packaged in a bag, then the bag placed inside a box, for sale to consumers. Printed on the box is a message stating, "Acrylamide-reduced!"

Example 12

Masa Flour with Enzyme

An effective amount of dried enzyme is mixed with a non-enzymatically treated, traditionally processed corn masa flour. This mixture is sold as an ingredient to be used to prepare corn masa-based food products. The mixture can be used to make food products having greater than 10% reduction in acrylamide.

Example 13

Article of Commerce

The masa flour with enzyme of Example 12 is packaged in a bag for sale. On the bag, instructions describe the appropriate conditions (time, temperature, pH) for use of the masa flour such that the resulting masa-based food product has greater than 10% reduction in acrylamide.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for removing asparagine or converting asparagine to a different substance by hydrolyzing the amide group of the asparagine to form aspartic acid in a corn-based food material comprising adding asparaginase enzyme to the food material before heating.

2. The method of claim 1, wherein at least about 10% of the asparagine is converted to a different substance or removed.

3. A method for removing asparagine or converting asparagine to a different substance by hydrolyzing the amide group of the asparagine to form aspartic acid in a corn-based food material, comprising:
   (1) adding asparaginase enzyme to the corn-based food material, wherein said corn based food material comprises asparagine;
   (2) optionally mixing the enzyme with the corn based food material;
   (3) allowing a sufficient time for the enzyme to react with the asparagine; and
   (4) optionally deactivating or optionally removing the enzyme.

4. A method for reducing the level of acrylamide formed in heated corn-based food products, comprising:
   (1) adding asparaginase to a corn-based food material, wherein said corn-based food material comprises asparagine;
   (2) optionally mixing the enzyme with the corn-based food material;
   (3) allowing a sufficient time for the enzyme to react with the asparagine whereby at least a portion of the asparagine is removed or is converted to a different substance by hydrolyzing the amide group of the asparagine to form aspartic acid;
   (4) optionally deactivating or optionally removing the enzyme; and
   (5) heating the corn-based food material to form the heated corn-based food product.

5. A corn-based food material prepared according to the method of claim 1, wherein at least about 10% of the asparagine is converted to a different substance or is removed.

6. A corn-based food material prepared according to the method of claim 1, wherein at least about 30% of the asparagine is converted to a different substance or is removed.

7. A corn-based food material prepared according to the method of claim 1, wherein at least about 50% of the asparagine is converted to a different substance or is removed.

8. A corn-based food material prepared according to the method of claim 1, wherein at least about 70% of the asparagine is converted to a different substance or is removed.

9. A corn-based food material prepared according to the method of claim 8, wherein at least about 90% of the asparagine is converted to a different substance or is removed.

* * * * *